United States Patent
Zhang et al.

(10) Patent No.: US 12,134,081 B2
(45) Date of Patent: Nov. 5, 2024

(54) CONTINUOUS PREPARATION SYSTEM AND METHOD FOR VINYLIDENE CHLORIDE

(71) Applicants: ZHEJIANG QUZHOU JUSU CHEMICAL INDUSTRY CO., LTD., Zhejiang (CN); BEIJING UNIVERSITY OF CHEMICAL TECHNOLOGY, Beijing (CN); JUHUA GROUP CO., LTD., Zhejiang (CN)

(72) Inventors: Liangliang Zhang, Beijing (CN); Liyang Zhou, Zhejiang (CN); Guangwen Chu, Beijing (CN); Jinyuan Lin, Zhejiang (CN); Jihong Tong, Zhejiang (CN); Jianfeng Chen, Beijing (CN); Yidong Zhang, Beijing (CN); Zhigang Wu, Zhejiang (CN); Yunfei Yu, Zhejiang (CN)

(73) Assignees: ZHEJIANG QUZHOU JUSU CHEMICAL INDUSTRY CO., LTD., Zhejiang (CN); BEIJING UNIVERSITY OF CHEMICAL TECHNOLOGY, Beijing (CN); JUHUA GROUP CO., LTD., Zhejiang (CN)

( * ) Notice: Subject to any disclaimer, the term of this patent is extended or adjusted under 35 U.S.C. 154(b) by 0 days.

(21) Appl. No.: 18/258,616

(22) PCT Filed: Dec. 24, 2021

(86) PCT No.: PCT/CN2021/141197
§ 371 (c)(1),
(2) Date: Jun. 21, 2023

(87) PCT Pub. No.: WO2022/135562
PCT Pub. Date: Jun. 30, 2022

(65) Prior Publication Data
US 2024/0033706 A1 Feb. 1, 2024

(30) Foreign Application Priority Data

Dec. 25, 2020 (CN) .......................... 202011563992.0

(51) Int. Cl.
*C07C 17/25* (2006.01)
*B01J 4/00* (2006.01)
(Continued)

(52) U.S. Cl.
CPC ............... *B01J 19/28* (2013.01); *B01J 4/001* (2013.01); *B01J 19/0006* (2013.01);
(Continued)

(58) Field of Classification Search
CPC ..................................................... C07C 17/25
See application file for complete search history.

(56) References Cited

FOREIGN PATENT DOCUMENTS

| CN | 106542596 | 3/2017 |
|---|---|---|
| CN | 107141239 A | 9/2017 |

(Continued)

OTHER PUBLICATIONS

Machine translation WO2018038460A1, Mar. 2018, pp. 1-14 (Year: 2018).*

(Continued)

*Primary Examiner* — Medhanit W Bahta
(74) *Attorney, Agent, or Firm* — RANKIN, HILL & CLARK LLP

(57) ABSTRACT

The present application provides a continuous preparation system and method for vinylidene chloride. In the present application, by coupling two stages of high gravity reactors, the product vinylidene chloride and water vapor are distilled from a reaction system in form of an azeotrope by adopting a water vapor steam stripping method, and the product obtained using the method has high purity. In addition, by combining steam stripping and high gravity, trichloroethane (Continued)

and alkali solution are rapidly mixed for mass transfer, and the product vinylidene chloride is rapidly distilled from the reaction system in form of the azeotrope (based on rapid diffusion of water vapor), such that the reaction proceeds continuously towards the direction of producing vinylidene chloride, thus significantly improving the conversion rate. As proved by a test apparatus, the present application can stabilize the purity of the vinylidene chloride product at 98% or more (mass fraction), decrease the TOC value of chloride salt wastewater to 100 mg/L or less, and decrease the consumption of materials and the cost of subsequent salt-containing wastewater treatment.

9 Claims, 1 Drawing Sheet

(51) Int. Cl.
  *B01J 19/00* (2006.01)
  *B01J 19/18* (2006.01)
  *B01J 19/28* (2006.01)

(52) U.S. Cl.
  CPC ........... *B01J 19/1856* (2013.01); *C07C 17/25* (2013.01); *B01J 2219/00038* (2013.01); *B01J 2219/00164* (2013.01)

(56) References Cited

FOREIGN PATENT DOCUMENTS

| | | | |
|---|---|---|---|
| CN | 108503519 | 9/2018 | |
| CN | 109126392 A | 1/2019 | |
| CN | 112774591 | 5/2021 | |
| TW | 201711964 A | 4/2017 | |
| WO | WO-2018038460 A1 * | 3/2018 | .............. B01J 19/00 |

OTHER PUBLICATIONS

Chinese Office Action (English and Chinese) of 202011563992.0 dated Feb. 25, 2022, 11 pages.
International Search Report (English and Chinese) and Written Opinion of PCT/CN2021/141197 dated Mar. 14, 2022, 12 pages.

* cited by examiner

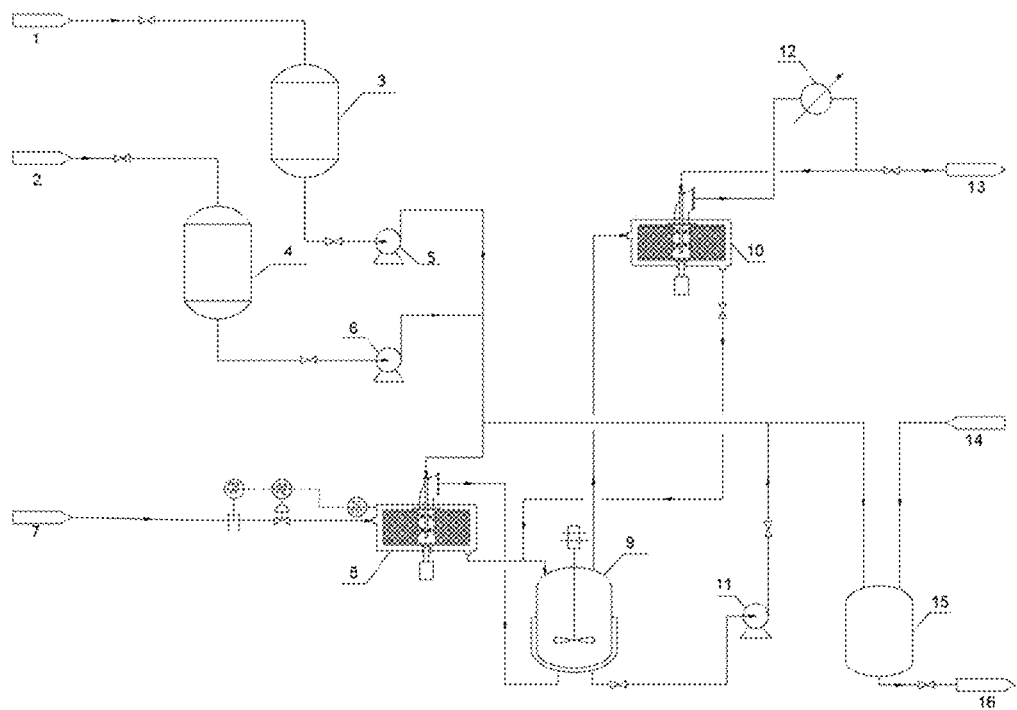

CONTINUOUS PREPARATION SYSTEM AND METHOD FOR VINYLIDENE CHLORIDE

TECHNICAL FIELD

The present application relates to the field of preparation of vinylidene chloride, in particular to a continuous preparation system and method for vinylidene chloride.

BACKGROUND

Vinylidene chloride, as an important polymer monomer, is the main monomer for producing polyvinylidene chloride (PVDC) resin and PVDC latex. It is also an important intermediate for producing chlorofluorocarbon substitutes and plays an important role in industries such as pharmaceuticals and fuels, with a wide range of application. Its polymers can be used for fibers, modified resins, coatings, adhesives, fireproof coatings, food and chemical packaging materials. At present, the liquid-phase saponification method of 1,1,2-trichloroethane is mainly used in China, but the existing saponification process of 1,1,2-trichloroethane is backward, resulting in low production capacity of equipment, high energy consumption, low VDC purity, and likelihood of producing byproduct chloroacetylene. Moreover, chloroacetylene is extremely unstable, and prone to decomposition, spontaneous combustion and even explosion when concentration accumulates, posing a certain threat to safety production. Therefore, it is necessary to improve the continuous reaction system for preparing vinylidene chloride in order to improve the production capacity of equipment and ensure the safety of the production process.

For the continuous reaction of 1,1,2-trichloroethane to prepare vinylidene chloride, saponification can be divided into sodium hydroxide process, calcium hydroxide process, and ammonium hydroxide process according to the different alkali used. The calcium hydroxide process is widely applied due to its low cost, low production of chloroacetylene, and relatively safe reaction. Its reaction equation is as follow:

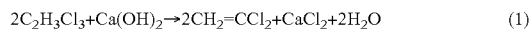   (1)

While 1,1,2-trichloroethane reacts with calcium hydroxide to produce vinylidene chloride, side reactions also occur to produce chloroacetylene, cis 1,2-dichloroethylene and trans 1,2-dichloroethylene as follows:

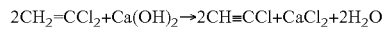

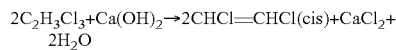

The main industrial production process currently involves the reaction of 1,1,2-trichloroethane and calcium hydroxide solution in a large stirred tank, followed by the separation of light and heavy components through multiple stages of distillation towers to obtain refined vinylidene chloride products and byproduct calcium chloride solution. Chinese patent CN 200310122646.9 discloses a method for preparing vinylidene chloride using multiple stages of stirred tanks in series to achieve high conversion rate. Chinese patent CN 201780050736.1 discloses a reaction kettle apparatus that uses a stirred tank with multiple stages of impellers to improve the reactivity of the reaction. However, the above methods all have problems such as high byproduct content, low conversion rate, high Total Organic Carbon (TOC) value in $CaCl_2$) wastewater, and there is no good solution in the industry.

SUMMARY

In order to solve at least one of the above problems, in one aspect, the present application provides a continuous preparation system for vinylidene chloride, wherein the continuous preparation system includes:

a first high gravity reactor, a liquid inlet of the first high gravity reactor being communicated with a liquid inlet pipeline of trichloroethane and alkali solution, a gas inlet of the first high gravity reactor being communicated with a water vapor pipeline;

a reaction kettle, an inlet of the reaction kettle being communicated with a liquid outlet of the first high gravity reactor, a gas inlet of the reaction kettle being communicated with a gas outlet of the first high gravity reactor, the reaction kettle being communicated with an external product storage tank through a first branch pipeline;

a second high gravity reactor, a liquid outlet of the second high gravity reactor being communicated with a liquid inlet of the reaction kettle, a gas inlet of the second high gravity reactor being communicated with a gas outlet of the reaction kettle; and a condensation circulation pipeline, the condensation circulation pipeline and a gas outlet and gas inlet of the second high gravity reactor forming a condensation loop.

In a preferred example, the reaction kettle is communicated with the liquid inlet of the first high gravity reactor through a second branch pipeline, and the continuous preparation system further includes:

a first valve located on the first branch pipeline; and
a second valve located on the second branch pipeline.

In a preferred example, the continuous preparation system further includes:

a valve controller coupled with the first valve and/or the second valve and configured to control the opening of the corresponding valve.

In a preferred example, the continuous preparation system further includes:

a detector configured to detect flow rate at the liquid inlet pipeline of trichloroethane and alkaline solution; and a processor configured to determine the opening of the corresponding valve according to the flow rate.

In a preferred example, the first high gravity reactor and the second high gravity reactor are rotating packed beds.

In a preferred example, oleophobic packings are provided in the rotating packed beds.

In a preferred example, a plurality of run-through micropores are formed in the oleophobic packings.

In a preferred example, the micropores are of micro-nano scale.

In a preferred example, the gas inlet of the first high gravity reactor is located in a sidewall of the first high gravity reactor and is directed to the inside of the packings.

The present application further provides a continuous preparation method for vinylidene chloride, wherein the continuous preparation method includes: preparing vinylidene chloride by using the continuous preparation system.

The Present Application has the Following Beneficial Effects

The present application provides a continuous preparation system and method for vinylidene chloride. In the present application, by coupling two stages of high gravity reactors, the product vinylidene chloride and water vapor are distilled from a reaction system in form of an azeotrope by adopting a water vapor steam stripping method, and the product obtained using the method has high purity. On the one hand, water vapor is replenished through an external water vapor source, and on the other hand, it can be recycled through reaction cycles to form a water vapor cycle, thus ensuring the amount of water vapor used and not requiring a large amount of water vapor. Further, the combination of the azeotrope with the multiple stages of high gravity reactors greatly improves the gas-phase and liquid-phase mass transfer efficiency of the azeotrope aiming at the feature of the azeotrope in the reaction system of the present application, thus improving the overall conversion rate of the reaction. In addition, by combining steam stripping and high gravity, trichloroethane and alkali solution are rapidly mixed for mass transfer, and the product vinylidene chloride is rapidly distilled from the reaction system in form of the azeotrope (based on rapid diffusion of water vapor), such that the reaction proceeds continuously towards the direction of producing vinylidene chloride, thus significantly improving the conversion rate. As proved by a test apparatus, the present application can stabilize the purity of the vinylidene chloride product at 98% or more (mass fraction), decrease the TOC value of chloride salt wastewater to 100 mg/L or less, and decrease the consumption of materials and the cost of subsequent salt-containing wastewater treatment.

DESCRIPTION OF THE DRAWINGS

In order to describe the examples of the present application or the technical solutions in the existing technologies more clearly, the drawings used in the description of the examples or existing technologies will be briefly introduced below. Obviously, the drawings in the following description are only some examples of the present application. Those skilled in the art may obtain other drawings according to these drawings without contributing any inventive labor.

The FIGURE illustrates a schematic diagram of a continuous preparation system for vinylidene chloride according to an example of the present application.

Description of reference signs in the FIGURE: 1—trichloroethane solution inlet; 2—calcium hydroxide solution inlet; 3—No.1 storage tank; 4—No.2 storage tank; 5—No.1 pump; 6—No.2 pump; 7—water vapor inlet; 8—first high gravity reactor; 9—stirred tank reactor; 10—second high gravity reactor; 11—circulating pump; 12—condenser; 13—product vinylidene chloride outlet; 14—neutralizer hydrochloric acid inlet; 15—regulating tank; 16—chloride salt wastewater outlet.

DESCRIPTION OF THE EMBODIMENTS

The technical solutions in the examples of the present application will be clearly and completely described with reference to the drawings in the examples of the present application. Obviously, the described examples are only a part of the examples of the present application, not all of them. All other examples obtained by those skilled in the art based on the examples of the present application without contributing any inventive labor still fall within the scope of protection of the present application.

As found by the inventor through research, at present, the mainstream production process for preparing vinylidene chloride involves the reaction of trichloroethane and calcium hydroxide solution in a large stirred tank, followed by the separation of light and heavy components through multiple stages of distillation towers to obtain refined vinylidene chloride products and byproduct calcium chloride solution. However, there are still many shortcomings, such as low product conversion rate and great likelihood of multiple side reactions. There is still no good solution in the industry. At the same time, industry researchers are unaware of the reason for the shortcomings, and research progress in related areas has been stagnant.

As found by the inventor through experimental exploration, the reason for the shortcomings is poor gas-liquid mixing in the stirred tank, resulting in insufficient contact between the oil and water phases. In addition, calcium hydroxide is very easy to stick and the pressure drop inside the reaction kettle is large, making it difficult to transfer products in time, resulting in low conversion rate and equipment blockage.

Moreover, due to the poor mixing effect of oil and water phases, excess of alkali at local positions is caused. Besides, the reaction time is long, making it easy for multiple side reactions to occur.

Details are as follows:
(1) The reaction efficiency is low and the reaction time is long. 1,1,2-trichloroethane and calcium hydroxide suspension are completely immiscible. 1,1,2-trichloroethane is a typical organic substance and an oil-phase liquid, while calcium hydroxide is slightly soluble in water and appears as an aqueous suspension in water. In the traditional stirred tank reactor, organic matters agglomerate in the form of large oil droplets and even are directly layered. However, some undissolved calcium hydroxide can also serve as adsorption nuclei in the reactor, and oil droplets aggregate on and coat the surface of calcium hydroxide micronuclei. Due to the poor mixing effect of organic matters and aqueous solution, the actual contact area of the two reactants is small, resulting in low reaction rate and long reaction time. According to research, the reaction time of the current mainstream process is up to 10 h.
(2) The separation effect is poor and the steam consumption is high. At present, distillation is used in the industry to refine products. Due to the low product content and high byproduct content in the outlet gas of the traditional stirred tank reactor, subsequent distillation separation consumes a large amount of energy. In the tank reactor used in the above patents, the gas-liquid contact area for stripping separation of vinylidene chloride is small, resulting in slow rate of vaporization of vinylidene chloride into the gas phase, poor separation effect, and high steam consumption.
(3) The volume of the stirred tank is large, the energy consumption is high and the investment is high. The reaction effect when using a single stirred tank is not ideal. Although using the multiple stages of stirred tanks in series mentioned in the above patents can improve the reaction efficiency, it greatly increases the volume of the reaction equipment, increases the energy consumption and increases the investment.
(4) The content of byproducts is high. The reaction is carried out in the traditional stirred tank. Since the oil phase 1,1,2-trichloroethane in the tank is not in full contact with the aqueous phase calcium hydroxide suspension, the alkali concentration distribution is uneven, and the produced vinylidene chloride cannot be separated from the reaction system in time due to poor separation effect, thus making vinylidene chloride further react with the alkali to produce chloroacetylene.

In addition, 1,1,2-trichloroethane will react synchronously to produce cis 1,2-dichloroethylene and trans 1,2-dichloroethylene. The longer the reaction time, the greater the cumulative amount of chloroacetylene, cis 1,2-dichloroethylene, and trans 1,2-dichloroethylene. Moreover, due to the poor separation effect and long reaction time of the traditional stirred tank, it is easy to cause the product vinylidene chloride to be self-polymerized to produce polyvinylidene chloride.

(5) The Total Organic Carbon (TOC) value in $CaCl_2$ wastewater is high. Due to poor mixing and separation efficiency in the traditional stirred tank, the reaction of reactant trichloroethane is incomplete. In addition, the produced vinylidene chloride cannot be extracted in time from the reaction to react with the alkaline solution to produce chloroacetylene, resulting in high TOC value in $CaCl_2$) wastewater and increasing the cost of subsequent wastewater treatment. According to the investigation, the TOC value in the $CaCl_2$) wastewater in the current mainstream process is about 150 mg/L.

In view of this, the present application provides a continuous preparation system for vinylidene chloride. Referring to the FIGURE, the continuous preparation system specifically includes:

a first high gravity reactor 8, a liquid inlet of the first high gravity reactor 8 being communicated with a liquid inlet pipeline of trichloroethane 1 and alkali solution 2, a gas inlet of the first high gravity reactor 8 being communicated with a water vapor pipeline;

a reaction kettle 9, an inlet of the reaction kettle 9 being communicated with a liquid outlet of the first high gravity reactor 9, a gas inlet of the reaction kettle 9 being communicated with a gas outlet of the first high gravity reactor 8, the reaction kettle 9 being communicated with an external product storage tank 15 through a first branch pipeline;

a second high gravity reactor 10, a liquid outlet of the second high gravity reactor 10 being communicated with a liquid inlet of the reaction kettle 9, a gas inlet of the second high gravity reactor 10 being communicated with a gas outlet of the reaction kettle 9; and a condensation circulation pipeline, the condensation circulation pipeline and a gas outlet and gas inlet of the second high gravity reactor 10 forming a condensation loop (for example, the condensation loop includes a condenser 12).

In the present application, by coupling two stages of high gravity reactors, the product vinylidene chloride and water vapor are distilled from a reaction system in form of an azeotrope by adopting a water vapor steam stripping method, and the product obtained using the method has high purity. On the one hand, water vapor is replenished through an external water vapor source, and on the other hand, it can be recycled through reaction cycles to form a water vapor cycle, thus ensuring the amount of water vapor used and not requiring a large amount of water vapor. Further, the combination of the azeotrope with the multiple stages of high gravity reactors greatly improves the gas-phase and liquid-phase mass transfer efficiency of the azeotrope aiming at the feature of the azeotrope in the reaction system of the present application, thus improving the overall conversion rate of the reaction. In addition, by combining steam stripping and high gravity, trichloroethane and alkali solution are rapidly mixed for mass transfer, and the product vinylidene chloride is rapidly distilled from the reaction system in form of the azeotrope (based on rapid diffusion of water vapor), such that the reaction proceeds continuously towards the direction of producing vinylidene chloride, thus significantly improving the conversion rate. As proved by a test apparatus, the present application can stabilize the purity of the vinylidene chloride product at 98% or more (mass fraction), decrease the TOC value of chloride salt wastewater to 100 mg/L or less, and decrease the consumption of materials and the cost of subsequent salt-containing wastewater treatment.

It is to be understood that the present application innovatively adopts the steam stripping method and reuses the water vapor required by the system itself as steam for steam stripping. On the one hand, it does not increase the equipment cost, only requires pipeline reconstruction. On the other hand, the steam stripping method is adopted to quickly remove the product in azeotropic form, which can quickly transfer the product, such that the reaction proceeds continuously towards the direction of producing vinylidene chloride, thus significantly improving the conversion rate.

In an example not illustrated in the FIGURE, the reaction kettle is communicated with the liquid inlet of the first high gravity reactor through a second branch pipeline, and the continuous preparation system further includes:

a first valve located on the first branch pipeline; and
a second valve located on the second branch pipeline.

In this example, by controlling the first value and the second valve, the flow rate returned to the first high gravity reactor and the flow rate of the product storage tank can be adjusted, thereby controlling the reaction balance of the entire reaction system and improving the overall reaction conversion rate.

Further, in some examples, the continuous preparation system further includes:

a valve controller coupled with the first valve and/or the second valve and configured to control the opening of the corresponding valve.

In this example, the opening of the valve can be automatically controlled through the valve controller, thus not requiring manual control.

Further, the continuous preparation system further includes:

a detector configured to detect flow rate at the liquid inlet pipeline of trichloroethane and alkaline solution; and a processor configured to determine the opening of the corresponding valve according to the flow rate.

In this example, the flow rate of the raw material inlet can be detected by the detector, and the opening of the valve can be adjusted based on the flow rate feedback. That is, the adjustment in this example is based on overall flow rate control, is pertinent and can achieve automatic and dynamic adjustment.

In addition, in the examples of the present application, the condensation circulation pipeline may further include a plurality of condensers, which will not be repeated in the present application.

In addition, in the present application, the high gravity reactor may be pertinently selected. The first high gravity reactor and the second high gravity reactor are rotating packed beds.

In this example, for the steam stripping of water vapor, the dispersion and mixing of the gas phase are emphasized, and the packings in the rotating packed beds are used for mass transfer and mixing, thus greatly improving the overall dispersion effect and the steam stripping effect. The stator and rotor are used for liquid reaction, thus increasing the collision area of the liquid and improving the liquid-phase reaction efficiency.

Further, in order to avoid blockage, the first high gravity reactor is a rotating packed bed, and an oleophobic packing is provided in the rotating packed bed.

It is to be understood that high gravity technology is a typical process intensification technology that has been successfully applied in various industrial processes that intensify mass transfer, heat transfer and micro mixing, and has achieved excellent results. It has the characteristics of small equipment floor area, short residence time, high mass transfer efficiency, and high reaction speed and efficiency.

The present application combines the high gravity technology with the steam stripping technology and applies it to the preparation process of vinylidene chloride. In the first high gravity reactor, the alkali solution and trichloroethane are fully mixed and react quickly. At the same time, under the action of water vapor, the reaction system undergoes sufficient turbulence and efficient mass and heat transfer. The product vinylidene chloride and water vapor are distilled from the reaction system in the form of an azeotrope, and the water vapor enters the first high gravity reactor to quickly remove the produced vinylidene chloride, so that the reaction proceeds towards the direction of producing vinylidene chloride, thus greatly suppressing the occurrence of side reactions. In addition, since the residence time of the product in the system is greatly shortened, the problem of product self-polymerization has been effectively solved.

The continuous preparation system provided by the present application will be described below in detail by taking the FIGURE as an example. Referring to the FIGURE, a process system for preparing vinylidene chloride through continuous reaction includes a first high gravity reactor (8), a stirred tank (9), a second high gravity reactor (10), a condenser (12), a No.1 storage tank (3), a No.2 storage tank (4), a regulating tank (15), a circulating pump (11), a No.1 pump (5) and a No.2 pump (6). The No.1 storage tank (3) and the No.2 storage tank (4) are respectively connected with a liquid inlet of the first high gravity reactor (8) through the No. pump (5) and the No.2 pump (6). A liquid outlet of the first high gravity reactor (8) is connected with a liquid inlet of the stirred tank (9). A liquid outlet of the stirred tank (9) is connected with an inlet of the circulating pump (11). An outlet of the circulating pump (11) is connected with a liquid inlet of the first high gravity reactor (8). A bypass is provided between the outlet of the circulating pump (11) and the liquid inlet of the first high gravity reactor (8). The bypass connects the outlet of the circulating pump (11) with a liquid inlet of the regulating tank (15). A liquid outlet of the regulating tank (15) is connected with a byproduct outlet (16). A neutralizer inlet (14) is connected with the liquid inlet of the regulating tank (15). A water vapor inlet (7) is connected with a gas inlet of the first high gravity reactor (8). A gas outlet of the first high gravity reactor (8) is connected with a gas inlet of the stirred tank (9). A gas outlet of the stirred tank (9) is connected with a gas inlet of the second high gravity reactor (10). A gas outlet of the second high gravity reactor (10) is connected with an inlet of the condenser (12. An outlet of the condenser (12) is connected with a product outlet (13). A bypass is provided between the outlet of the condenser (12) and the product outlet (13). The bypass connects the outlet of the condenser (12) with a liquid inlet of the second high gravity reactor (10).

A process method matching the process system is specifically as follows: reaction material liquid is crushed into small droplets and emulsion droplets in the first high gravity reactor, which are quickly mixed in the reactor; in the second high gravity reactor, gasified crude products and reflux condensate are fully in contact for rapid heat and mass transfer, so as to achieve efficient separation of light and heavy components.

More specifically, the process method mainly includes the following steps:

a. Raw materials 1,1,2-trichloroethane and alkaline solution are continuously added to the first high gravity reactor according to a certain ratio, and are fully mixed for rapid reaction. At the same time, water vapor is continuously fed into the first high gravity reactor to exchange heat with the reaction material liquid.

b. The product vinylidene chloride and partially unreacted trichloroethane in the material liquid of the first high gravity reactor are heated and gasified, then carried out by water vapor from the top of the first high gravity reactor, and then are fed into the stirred tank from the bottom of the stirred tank. The remaining material liquid in the first high gravity reactor flows out from the bottom of the reactor and then flows into the stirred tank from the top.

c. The gas and liquid discharged from the first high gravity reactor are in countercurrent contact in the stirred tank for full mass and heat transfer. Most of trichloroethane entrained in the gas is washed into the liquid phase, and most of dissolved vinylidene chloride in the liquid is stripped into the gas phase by steam. After contacting, the gas is discharged from the top of the stirred tank and the liquid is discharged from the bottom of the stirred tank.

d. The liquid (mainly mixed solution of byproduct chloride and trichloroethane and alkali that have not yet fully reacted) discharged from the bottom of the stirred tank is divided into two streams according to a certain ratio. One stream is used as circulating liquid and is circulated back to the first high gravity reactor through the circulating pump. The other stream is used as solution of byproduct chloride, is neutralized by hydrochloric acid and then is extracted.

e. The gas (mainly water vapor, vaporized vinylidene chloride, and a small amount of entrained trichloroethane) discharged from the top of the stirred tank is fed into the second high gravity reactor, where it fully contacts and is mixed with the reflux condensate. The heavy component is liquefied under the cooling of the reflux liquid in the second high gravity reactor, is discharged from the bottom of the second high gravity reactor, and is fed into the stirred tank as circulating liquid. The light component is discharged from the top of the second high gravity reactor in a gasified state.

f. The light component gas discharged from the top of the second high gravity reactor passes through the condenser and becomes liquid of the product vinylidene chloride. Then, the liquid is divided into two streams according to a certain ratio. One stream is fed into the second high gravity reactor as circulating liquid, which is used as the reflux condensate. The other stream is extracted as the vinylidene chloride product.

Specifically, the high gravity field level in the first high gravity reactor is 30-1500 g, preferably 50-300 g. The reaction temperature in the first high gravity reactor is 50-100° C. The alkali solution includes but is not limited to calcium hydroxide solution, sodium hydroxide solution, ammonia water or a mixture thereof. The feed molar ratio of 1,1,2-trichloroethane to alkali solution is 1.1-2:1, preferably 1.1-1.7:1. The amount of water vapor continuously fed into the first high gravity reactor is 110-160 Kg/(t VDC). In the reaction process, the vacuum degree of the control system is 60-100 Kpa, preferably 70-90 Kpa. The ratio of the flow rate of the circulating liquid to the flow rate of the extracted liquid divided from the liquid discharged from the bottom of the stirred tank is 2-10:1, preferably 4-8:1. The ratio of the flow rate of the circulating liquid to the flow rate of the extracted product liquid divided from the liquid of the product vinylidene chloride obtained after the light component gas discharged from the top of the second high gravity reactor passes through the condenser is 3-4:1.

It is to be understood that the present application has the following detailed effects due to the combination of high gravity equipment with water vapor steam stripping:

(1) The first high gravity reactor in the present application, on the one hand, can quickly mix the two streams of reaction liquid of oil phase and water phase and break them into small liquid droplets and emulsion droplets for full contact, and can effectively prevent pipeline blockage when the used alkali liquid is calcium hydroxide suspension. On the other hand, through the continuous shearing crushing of the high gravity packing to destroy the oil droplets coated on calcium hydroxide particles, the calcium hydroxide as the reactant raw material is fully stripped out and rapidly dissolved after continuous contact with water, thus facilitating the occurrence of the reaction. The second high gravity reactor in the present application can effectively facilitate gas-liquid contact and separation, thus obtaining high-purity vinylidene chloride products. The efficient coupling of the first high gravity reactor and the second high gravity reactor can achieve very good results in the continuous reaction process for preparing vinylidene chloride.

(2) The reaction efficiency is improved and the reaction time is shortened. The system in the present application integrates reaction, separation and purification, and can achieve rapid and uniform mixing and reaction of 1,1,2-trichloroethane solution and calcium hydroxide solution in the first high gravity reactor. After further separation and purification in the stirred tank, gas-liquid two-phase rapid contact and separation are carried out in the second high gravity reactor to obtain high-purity vinylidene chloride product. Therefore, by adopting the system and method provided by the present application, the reaction rate can be greatly improved, and it is conservatively believed that the reaction time is shortened by more than three times compared with the traditional stirred tank, thus helping to improve the production capacity in future.

(3) The occurrence of side reactions is inhibited and the content of byproducts is reduced. The first high gravity reactor and the second high gravity reactor in the present application can significantly improve the reaction and separation rates, and significantly shorten the reaction time. Since the reaction rates of the above side reactions are slow, the reaction time is shortened, thus effectively inhibit the production of byproducts. At the same time, the alkali concentration distribution is relatively uniform, thus effectively preventing the product vinylidene chloride from excessively reacting to produce chloroacetylene due to the local high alkali concentration in the traditional stirred tank. Moreover, water vapor is fed into the first high gravity reactor to quickly remove the produced vinylidene chloride, so that the reaction proceeds towards the direction of producing vinylidene chloride, thus greatly inhibiting the occurrence of side reactions. In addition, since the residence time of the product in the system is greatly shorted, the problem of product self-polymerization has been effectively solved.

(4) The purity of vinylidene chloride is improved. The system in the present application integrates reaction, separation and purification. The second high gravity reactor in the present application can achieve full reverse contact, separation and purification of gas-liquid phases. The condensed liquid phase partially flows back to the second high gravity reactor to achieve the purpose of further refining vinylidene chloride. The liquid phase at the outlet of the second high gravity reactor is recycled back to the first high gravity reactor for reaction, thus achieving a very good purification effect of vinylidene chloride. The present application can stabilize the purity of vinylidene chloride products above 98% (mass fraction).

(5) The steam consumption is reduced. The system in the present application integrates reaction, separation and purification. Compared with the traditional stirred tank reactor, the steam stripping process is carried out in the first high gravity reactor, and continuous countercurrent can achieve the effect of multiple stages of plates. Moreover, under the action of the packing, the liquid is highly crushed, the gas-liquid contact area is greatly increased, and the water vapor separation effect can be greatly improved, thus reducing the steam consumption. After the water vapor passing through the first high gravity reactor entrains the vaporized vinylidene chloride and a small amount of trichloroethane and enters the second high gravity reactor, it comes into countercurrent contact with the reflux condensate. Under the action of the packing, the liquid is highly crushed, the gas-liquid contact area is greatly increased, the light component in the liquid is gasified, the heavy component in the gas is condensed, and then the gas and liquid are quickly separated to obtain high-purity vinylidene chloride products. In the two stages of high gravity reactors, the heat and kinetic energy of steam are fully utilized.

(6) The equipment size, energy consumption and investment are reduced. The system in the present application integrates reaction, separation and purification, and can reduce the total volume of the device by more than three times compared with the traditional single stirred tank or multiple stages of stirred tank reactors in series. In addition, due to the efficient separation effect of the present application, the comprehensive energy consumption per unit product is reduced by about twice compared with the traditional stirred tank reactor.

(7) The TOC (mg/L) value of chloride wastewater is reduced. The system in the present application integrates reaction, separation and purification. The first high gravity reactor in the present application can achieve full mixing and reaction between two liquid phases, making trichloroethane react completely. The second high gravity reactor in the present application can achieve the purification and refinement of vinylidene chloride and further reflux reaction with 1,1,2-trichloroethane, thus significantly improving the conversion rate of 1,1,2-trichloroethane, reducing the content of byproducts, reducing the TOC value of chloride wastewater to 100 mg/L or less, and reducing the consumption of materials and the cost of subsequent salt-containing wastewater treatment.

The present application will be described through the following specific examples.

Example 1

A system for preparing vinylidene chloride through continuous reaction provided by the present application was adopted. The reed molar ratio (a) of 1,1,2-trichloroethane to calcium hydroxide solution was 1.4:1. The reaction temperature (T) was 80° C. The high gravity level ($G_1$) of the first high gravity reactor was 200 g. The high gravity level ($G_2$) of the second high gravity reactor was 200 g. The reaction vacuum degree (P) was 90 Kpa. The ratio (P) of the flow rate of the circulating liquid to the flow rate of the extract liquid divided from the liquid flowing from the bottom of the stirred tank was 5:1. The ratio (y) of the flow rate of the reflux condensate and the flow rate of the extracted product liquid divided from the liquid at the inlet of the condenser was 4:1. The total test time (t) was 150 min. The measured conversion rate was 99.95%. The VDC selectivity was 99.1%. The VDC purity was 98.5%. The amount (Q) of used water vapor was 130 Kg/(t VDC). The TOC value in $CaCl_2$ wastewater was 98 mg/L.

Examples 2-16: the process flow and steps are the same as those in example 1. See Table 1 for the process conditions, operating conditions and corresponding test results of each example. The meanings of the letters listed in the header are the same as those in example 1.

by coupling two stages of high gravity reactors, the product vinylidene chloride and water vapor are distilled from a reaction system in form of an azeotrope by adopting a water vapor steam stripping method, and the product obtained using the method has high purity. On the one hand, water vapor is replenished through an external water vapor source, and on the other hand, it can be recycled through reaction cycles to form a water vapor cycle, thus ensuring the amount of water vapor used and not requiring a large amount of water vapor. Further, the combination of the azeotrope with the multiple stages of high gravity reactors greatly improves the gas-phase and liquid-phase mass transfer efficiency of the azeotrope aiming at the feature of the azeotrope in the reaction system of the present application, thus improving the overall conversion rate of the reaction. In addition, by combining steam stripping and high gravity, trichloroethane and alkali solution are rapidly mixed for mass transfer, and the product vinylidene chloride is rapidly distilled from the reaction system in form of the azeotrope (based on rapid diffusion of water vapor), such that the reaction proceeds continuously towards the direction of producing vinylidene

TABLE 1

Process conditions and test results of examples 2-16

| Example | α | T/° C. | $G_1$/g | $G_2$/g | t/min | β | γ | Conversion rate/% | Selectivity/% | Purity/% | Q/Kg/(t VDC) | TOC/ mg/L |
|---|---|---|---|---|---|---|---|---|---|---|---|---|
| 2 | 1.7:1 | 80 | 200 | 200 | 150 | 4:1 | 4:1 | 99.98 | 99.2 | 98.9 | 130 | 95 |
| 3 | 1.4:1 | 60 | 200 | 200 | 150 | 4:1 | 4:1 | 99.02 | 98.2 | 98.9 | 135 | 95 |
| 4 | 1.4:1 | 80 | 300 | 200 | 150 | 4:1 | 4:1 | 99.99 | 99.8 | 99.2 | 150 | 65 |
| 5 | 1.4:1 | 80 | 200 | 200 | 150 | 4:1 | 4:1 | 99.90 | 98.9 | 98.7 | 160 | 93 |
| 6 | 1.4:1 | 80 | 200 | 200 | 90 | 4:1 | 4:1 | 99.88 | 99.0 | 98.2 | 129 | 98 |
| 7 | 1.4:1 | 80 | 200 | 200 | 150 | 7:1 | 4:1 | 99.99 | 99.5 | 99.4 | 160 | 85 |
| 8 | 1.4:1 | 80 | 200 | 200 | 150 | 1:1 | 4:1 | 95.93 | 92.3 | 89.2 | 97 | 198 |
| 9 | 2.2:1 | 80 | 200 | 200 | 150 | 4:1 | 4:1 | 99.99 | 92.2 | 98.8 | 230 | 70 |
| 10 | 1.4:1 | 100 | 200 | 200 | 150 | 4:1 | 4:1 | 99.99 | 85.2 | 97.2 | 190 | 85 |
| 11 | 1.4:1 | 80 | 20 | 200 | 150 | 4:1 | 4:1 | 86.52 | 84.2 | 95.7 | 500 | 650 |
| 12 | 1.4:1 | 80 | 200 | 20 | 150 | 4:1 | 4:1 | 99.82 | 90.2 | 90.4 | 300 | 170 |
| 13 | 1.4:1 | 80 | 200 | 200 | 30 | 4:1 | 4:1 | 89.2 | 90.3 | 95.2 | 130 | 240 |
| 14 | 1.4:1 | 80 | 200 | 200 | 150 | 4:1 | 4:1 | 97.51 | 97.2 | 97.5 | 300 | 102 |
| 15 | 1.4:1 | 80 | 200 | 200 | 150 | 4:1 | 6:1 | 99.98 | 99.2 | 99.8 | 320 | 85 |
| 16 | 1.4:1 | 80 | 200 | 200 | 150 | 4:1 | 1:1 | 99.98 | 98.2 | 94.9 | 115 | 150 |

Among all examples, the process parameters of examples 1-7 are within the process parameter ranges claimed by the present application. From the results of the examples, it can be concluded that the present application can not only improve the reaction efficiency, shorten the reaction time and reduce the device size, but also inhibit the occurrence of side reactions, reduce the content of byproducts, improve the purity of vinylidene chloride, reduce the steam consumption, and reduce the TOC value in $CaCl_2$ wastewater.

Among all examples, partial process and operating parameters of examples 8-16 are out of the process parameter ranges claimed by the present application. From the results of the examples, it can be concluded that deviating from the process and operating parameter ranges claimed by the present application will lead to a decrease in the conversion rate, selectivity and product purity, and an increase in the organic matter content in the wastewater; or the steam consumption is increased under the situation of reaching the equivalent technical level.

Further, the present application further provides a continuous preparation method for vinylidene chloride. The continuous preparation method includes: preparing vinylidene chloride by using the continuous preparation system.

The present application provides a continuous preparation method for vinylidene chloride. In the present application, chloride, thus significantly improving the conversion rate. As proved by a test apparatus, the present application can stabilize the purity of the vinylidene chloride product at 98% or more (mass fraction), decrease the TOC value of chloride salt wastewater to 100 mg/L or less, and decrease the consumption of materials and the cost of subsequent salt-containing wastewater treatment.

The various examples in the description are described in a progressive manner. For the same and similar parts in the examples, mutual reference may be made. Each example focuses on the difference from other examples. Especially for the system example, due to its basic similarity to the method example, the description is relatively simple. For relevant details, please refer to the description of the method example.

In the description, the reference terms "an implementation", "some implementations", "examples", "specific examples", or "some examples" refer to that the specific features, structures, materials, or characteristics described in combination with the implementation or example are included in at least one implementation or example in the description. The schematic expressions of the above terms in the description do not necessarily refer to the same implementation or example.

In addition, those skilled in the art may combine different implementations or examples described in the description and the features of different implementations or examples without causing mutual contradiction. The above description only describes the examples of the present application and is not intended to limit the examples of the present application. Those skilled in the art may make various changes and variations to the examples of the present application. Any modifications, equivalent replacements, improvements and the like made within the spirit and principle of the present application shall be included within the scope of the claims of the present application.

The invention claimed is:

1. A continuous preparation method for vinylidene chloride, applied to a continuous preparation system for vinylidene chloride, wherein the continuous preparation system comprises:
   a first high gravity reactor, a liquid inlet of the first high gravity reactor being communicated with a liquid inlet pipeline of trichloroethane and alkali solution, a gas inlet of the first high gravity reactor being communicated with a water vapor pipeline;
   a stirred tank, a liquid inlet of the stirred tank being communicated with a liquid outlet of the first high gravity reactor, a gas inlet of the stirred tank being communicated with a gas outlet of the first high gravity reactor, the stirred tank being communicated with an external product storage tank through a first branch pipeline;
   a second high gravity reactor, a liquid outlet of the second high gravity reactor being communicated with a liquid inlet of the stirred tank, a gas inlet of the second high gravity reactor being communicated with a gas outlet of the stirred tank; and
   a condensation circulation pipeline, the condensation circulation pipeline and a gas outlet and gas inlet of the second high gravity reactor forming a condensation loop;
   the continuous preparation method includes the following steps:
   a. raw materials 1,1,2-trichloroethane and alkaline solution are continuously added to the first high gravity reactor according to a certain ratio, and are fully mixed for rapid reaction; at the same time, water vapor is continuously fed into the first high gravity reactor to exchange heat with the reaction material liquid;
   b. the product vinylidene chloride and unreacted 1,1,2-trichloroethane in the material liquid of the first high gravity reactor are heated and gasified, then carried out by water vapor from the top of the first high gravity reactor, and then are fed into the stirred tank from the bottom of the stirred tank; remaining material liquid, which remains in the first high gravity reactor after the product vinylidene chloride and the unreacted 1,1,2-trichloroethane in the material liquid of the first high gravity reactor are heated and gasified, flows out from the bottom of the reactor and then flows into the stirred tank from the top;
   c. the gas and liquid discharged from the first high gravity reactor are in countercurrent contact in the stirred tank for full mass and heat transfer, most of trichloroethane entrained in the gas is washed into the liquid phase, and most of dissolved vinylidene chloride in the liquid is stripped into the gas phase by steam, after contacting, the gas is discharged from the top of the stirred tank and the liquid is discharged from the bottom of the stirred tank;
   d. the liquid discharged from the bottom of the stirred tank is divided into two streams according to a certain ratio, one stream is used as circulating liquid and is circulated back to the first high gravity reactor through the circulating pump, the other stream is used as solution for chloride, which is a byproduct of the reaction of the 1,1,2-trichloroethane and the alkaline solution, to produce a byproduct chloride solution, and the byproduct chloride solution is neutralized by hydrochloric acid and then is extracted;
   e. the gas discharged from the top of the stirred tank is fed into the second high gravity reactor, where it fully contacts and is mixed with reflux condensate to separate a heavy component and a light component; the heavy component is liquefied under the cooling of the reflux liquid in the second high gravity reactor, is discharged from the bottom of the second high gravity reactor, and is fed into the stirred tank as circulating liquid; the light component is discharged from the top of the second high gravity reactor in a gasified state; and
   f. the light component gas discharged from the top of the second high gravity reactor passes through a condenser and becomes liquid of the product vinylidene chloride, then, the liquid is divided into two streams according to a certain ratio, one stream is fed into the second high gravity reactor as circulating liquid, which is used as the reflux condensate, the other stream is extracted as the vinylidene chloride product.

2. The continuous preparation method according to claim 1, wherein the stirred tank is communicated with the liquid inlet of the first high gravity reactor through a second branch pipeline, and the continuous preparation system further comprises:
   a first valve located on the first branch pipeline; and
   a second valve located on the second branch pipeline.

3. The continuous preparation method according to claim 2, wherein the continuous preparation system further comprises:
   a valve controller coupled with the first valve and/or the second valve and configured to control the opening of the corresponding valve.

4. The continuous preparation method according to claim 3, wherein the continuous preparation system further comprises:
   a detector configured to detect flow rate at the liquid inlet pipeline of trichloroethane and alkaline solution; and
   a processor configured to determine the opening of the corresponding valve according to the flow rate.

5. The continuous preparation method according to claim 1, wherein the first high gravity reactor and the second high gravity reactor are rotating packed beds.

6. The continuous preparation method according to claim 5, wherein oleophobic packings are provided in the rotating packed beds.

7. The continuous preparation method according to claim 6, wherein a plurality of run-through micropores are formed in the oleophobic packings.

8. The continuous preparation method according to claim 1, wherein the micropores are of micro-nano scale.

9. The continuous preparation method according to claim 1, wherein the gas inlet of the first high gravity reactor is located in a sidewall of the first high gravity reactor and is directed to the inside of the packings.

* * * * *